United States Patent
Assaker

(10) Patent No.: US 7,819,920 B2
(45) Date of Patent: Oct. 26, 2010

(54) VERTEBRAL REPLACEMENT AND DISTRACTION DEVICE FOR PLACING SAID IMPLANT

(75) Inventor: Richard Assaker, Kain (BE)

(73) Assignee: Alphatec Spine, Inc., Carlsbad, CA (US)

( * ) Notice: Subject to any disclaimer, the term of this patent is extended or adjusted under 35 U.S.C. 154(b) by 778 days.

(21) Appl. No.: 10/543,691

(22) PCT Filed: Feb. 5, 2004

(86) PCT No.: PCT/FR2004/000262

§ 371 (c)(1),
(2), (4) Date: Oct. 17, 2005

(87) PCT Pub. No.: WO2004/071355

PCT Pub. Date: Aug. 26, 2004

(65) Prior Publication Data

US 2006/0200244 A1    Sep. 7, 2006

(30) Foreign Application Priority Data

Feb. 5, 2003    (FR) .................................. 03 01339

(51) Int. Cl.
*A61F 2/44* (2006.01)
(52) U.S. Cl. .................... 623/17.11; 606/246; 606/279; 623/17.12; 623/17.13; 623/17.14; 623/17.15; 623/17.16
(58) Field of Classification Search ............... 623/17.11, 623/17.13, 17.15, 17.16, 23.47; 606/61, 606/246, 279

See application file for complete search history.

(56) References Cited

U.S. PATENT DOCUMENTS

| | | | | | |
|---|---|---|---|---|---|
| 8,486 | A | * | 11/1851 | Hammitt | 108/3 |
| 3,987,499 | A | * | 10/1976 | Scharbach et al. | 623/17.11 |
| 4,078,441 | A | * | 3/1978 | Mazur | 74/99 R |
| 4,401,112 | A | * | 8/1983 | Rezaian | 606/279 |
| 4,553,273 | A | * | 11/1985 | Wu | 623/23.45 |
| 4,807,888 | A | * | 2/1989 | Pidde et al. | 273/392 |
| 4,863,476 | A | * | 9/1989 | Shepperd | 623/17.15 |
| 5,253,637 | A | * | 10/1993 | Maiden | 126/696 |
| 5,571,192 | A | * | 11/1996 | Schonhoffer | 623/17.11 |
| 5,989,290 | A | * | 11/1999 | Biedermann et al. | 623/17.11 |
| 6,045,579 | A | * | 4/2000 | Hochshuler et al. | 623/17.16 |
| 6,176,881 | B1 | * | 1/2001 | Schar et al. | 623/17.11 |
| 6,176,882 | B1 | * | 1/2001 | Biedermann et al. | 623/17.15 |

(Continued)

FOREIGN PATENT DOCUMENTS

DE    198 56 013    6/2000

(Continued)

*Primary Examiner*—Thomas C Barrett
*Assistant Examiner*—Christian Sevilla
(74) *Attorney, Agent, or Firm*—Michael R. Shevlin

(57) ABSTRACT

A vertebral replacement implant includes two longitudinal elements slidably mounted with respect to each other, and locking elements. These locking elements include, on one of the longitudinal elements, an anchor surface, and on the other of the longitudinal elements, an anchor shoe guided in translation to take up a first position in which the elements slide freely with respect to each other, and a second position in which the anchor shoe cooperates with the anchor surface to lock the elements together, with a system converting a rotational movement into a translational movement transmitted to the anchor shoe.

10 Claims, 3 Drawing Sheets

U.S. PATENT DOCUMENTS

| | | | |
|---|---|---|---|
| 6,190,413 B1 * | 2/2001 | Sutcliffe | 623/17.11 |
| 6,193,755 B1 * | 2/2001 | Metz-Stavenhagen et al. | 623/17.11 |
| 6,375,683 B1 * | 4/2002 | Crozet et al. | 623/17.15 |
| 6,454,806 B1 * | 9/2002 | Cohen et al. | 623/17.15 |
| 6,524,341 B2 * | 2/2003 | Lang et al. | 623/17.15 |
| 6,616,695 B1 * | 9/2003 | Crozet et al. | 623/17.11 |
| 6,723,126 B1 * | 4/2004 | Berry | 623/17.11 |
| 6,730,088 B2 * | 5/2004 | Yeh | 606/247 |
| 6,808,538 B2 * | 10/2004 | Paponneau | 623/17.16 |
| 6,866,682 B1 * | 3/2005 | An et al. | 623/17.15 |
| 7,018,415 B1 * | 3/2006 | McKay | 623/17.15 |
| 2002/0082696 A1 * | 6/2002 | Harms et al. | 623/17.11 |
| 2003/0045877 A1 * | 3/2003 | Yeh | 606/61 |
| 2004/0049271 A1 * | 3/2004 | Biedermann et al. | 623/17.11 |
| 2004/0181283 A1 * | 9/2004 | Boyer et al. | 623/17.11 |
| 2004/0220582 A1 | 11/2004 | Keller | |
| 2005/0085910 A1 * | 4/2005 | Sweeney | 623/17.11 |
| 2005/0113921 A1 * | 5/2005 | An et al. | 623/17.11 |
| 2006/0058877 A1 * | 3/2006 | Gutlin et al. | 623/17.11 |
| 2006/0064167 A1 * | 3/2006 | Keller | 623/17.11 |
| 2006/0074490 A1 * | 4/2006 | Sweeney | 623/17.15 |
| 2007/0191954 A1 * | 8/2007 | Hansell et al. | 623/17.15 |
| 2007/0255407 A1 * | 11/2007 | Castleman et al. | 623/17.11 |
| 2007/0270968 A1 * | 11/2007 | Baynham et al. | 623/17.11 |
| 2008/0004705 A1 * | 1/2008 | Rogeau et al. | 623/17.16 |

FOREIGN PATENT DOCUMENTS

| | | |
|---|---|---|
| WO | WO 9849975 A1 * | 11/1998 |
| WO | 99/63913 | 12/1999 |
| WO | 02/071986 | 9/2002 |

* cited by examiner

VERTEBRAL REPLACEMENT AND DISTRACTION DEVICE FOR PLACING SAID IMPLANT

This application is a filing under 35 USC 371 of PCT/FR2004/000262 filed Feb. 5, 2004.

BACKGROUND OF THE INVENTION

The present invention pertains to a medical implant intended to replace a vertebra, at least in part, with a view to maintaining the normal spacing between the adjacent vertebrae.

The subject of the invention finds application for vertebral replacement in the cervical, thoracic or lumbar region.

In the prior art, various variants are known for fabricating a replacement implant also called a corporectomy implant. Patent application FR 2 730 158 for example describes a spacer implant comprising two telescoping hollow elements having complementary shapes on their mutually opposite faces which engage to allow distraction movement of the elements while preventing their compression movement.

Said spacer implant makes it possible to adjust the length of the implant in situ while ensuring relative distancing between the two elements by sliding the elements as far as their final locking position. Said implant therefore has irreversible locking preventing any possible withdrawal which is a major drawback under certain inserting conditions.

Document WO 00/23 013 describes an implant comprising two hollow longitudinal elements, male and female, slidably mounted with respect to each other. This replacement implant comprises a coupling ring intended to take up a first position of non-engagement with complementary coupling means to allow free sliding of the elements with respect to each other, and a second position when it engages with the complementary coupling means to ensure locking of the elements together. The main disadvantage of said replacement implant pertains to the difficulty in rotationally commanding the coupling ring to change over from one position to the other.

SUMMARY OF THE INVENTION

The object of the invention is to overcome these prior art shortcomings by proposing a vertebral replacement implant designed to allow its length adjustment in situ while permitting possible fast, easy, reversible changeover from a length adjustment position to a locking position.

To achieve this objective, the vertebral replacement implant comprises:
  two hollow longitudinal elements, so-called male and female, slidably mounted with respect to one another along a common longitudinal axis,
  and means ensuring the locking and free sliding of the elements between each other,
According to the invention, the locking means comprise:
  on one of the elements, an anchor surface arranged on a longitudinal part of said element,
  and on the other element:
    an anchor shoe guided in translation to take up a first position in which the elements slide freely in relation to one another, and a second position in which the anchor shoe cooperates with the anchor surface to lock the elements together,
    a system for converting a rotational movement into a translational movement transmitted to the anchor shoe, the movement conversion system being provided with means for receiving an instrument for rotational command in the two opposite directions so that the anchor shoe takes up one of its positions in relation to the direction of the rotational command.

Advantageously, the movement conversion system is of screw/nut type.

According to one preferred characteristic of embodiment, the conversion system of screw/nut type comprises a pin guided in rotation and locked in translation, this pin being provided with a threaded part cooperating with tapping on the anchor shoe guided in translation and locked in rotation.

Advantageously, the pin extends diametrically inside the male element and comprises:
  a first end provided with the means for receiving the command instrument, this first end being guided in rotation and locked in translation in one wall of the male element,
  a second end provided with the threaded part cooperating with the tapping of the anchor shoe, guided in translation and locked in rotation in the opposite wall of the male element.

Advantageously, the means for receiving the command instrument lead into a lumen arranged in a wall of the female element to be accessible from outside the implant; the wall of the female element, on the inside in its part opposite the part provided with the lumen, being provided with the anchor surface.

Preferably, each male and female element is provided with an end wall intended to cooperate with a vertebral plateau.

A further object of the invention is to propose a replacement implant with which to optimise the contact between at least one of the end walls of the implant and the vertebral plateau. To achieve this objective, at least one end wall is equipped with an inclining system in the sagittal plane.

Advantageously, the inclining system is of screw/nut type and comprises a threaded rod guided in rotation and locked in translation, to cooperate with a tapped ring locked in rotation and connected to the end wall guided in its incline.

Advantageously the threaded rod extends diametrically inside an element and comprises means for receiving a command instrument accessible from outside the element.

A further object of the invention is to propose a distractor adapted to ensure the relative sliding between the male and female elements of the implant of the invention, even with a limited portal.

For this purpose the replacement implant, for each male and female element, comprises a grasping zone for a distractor ensuring the relative sliding between the male and female elements, these grasping zones being formed of two flats extending in diametrically opposite fashion on the male and female elements.

According to a further object of the invention, the distractor for inserting the replacement implant of the invention comprises:
  two jaws adapted to ensure the gripping of the male and female elements, mounted with mobile relative spacing,
  and a system for converting a rotational movement imposed by a handle into a jaw separating movement.

According to the invention, one of the jaws is fixedly mounted whilst the other jaw is mobile mounted at a relative distance from the fixed jaw, and in that the movement conversion system is performed by a rack connected to the mobile jaw and cooperating with a toothed wheel connected by a command rod to a handle.

According to another characteristic of embodiment, the movement conversion system is equipped with a no-return device preventing movement in an opposite direction to the separating of the male and female elements.

Advantageously the no-return device can be released, allowing movement in the direction in which the male and female elements are drawn together.

BRIEF DESCRIPTION OF THE DRAWINGS

Various other characteristics will become apparent from the following description with reference to the appended drawings showing non-limitative examples of embodiment of the subject of the invention.

DESCRIPTION OF THE PREFERRED EMBODIMENTS

Figure 1:
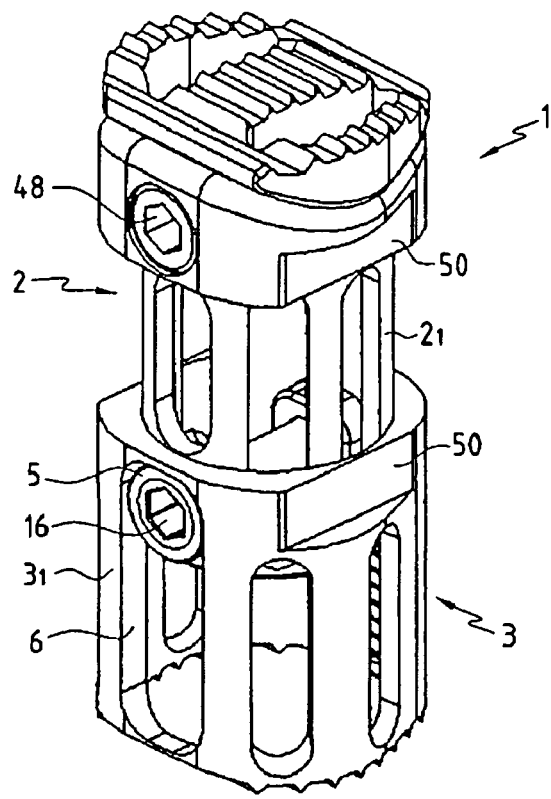
FIG. 1 is a perspective view showing an example of embodiment of an implant of the invention.

As shown more precisely FIGS. 1 to 4, the subject of the invention concerns a vertebral replacement implant 1 comprising a first so-called male hollow longitudinal element 2 and a second so-called female hollow longitudinal element 3. Each element 2, 3 respectively comprises a body $2_1$, $3_1$ of general tubular shape extending along a longitudinal axis X. The male body $2_1$ is adapted to engage partly inside the female body $3_1$ so that they extend co-axially in relation to one another. The male body $2_1$ has an outer casing of substantially identical shape and section, allowing clearance, to the inner bore delimited by the female body $3_1$. Preferably, the male $2_1$ and female $3_1$ bodies comprise recesses 4 for passing bone anchor volume.

According to one characteristic of the invention, the male 2 and female 3 elements are slidably mounted with respect to each other along their common longitudinal axis X. In the illustrated example, the sliding assembly between the male 2 and female 3 elements is made via a guiding abutment 5 fitted to the male element 2 and engaged in an open lumen 6 arranged on the female element 3 along a longitudinal direction parallel to the longitudinal axis X.

Figure 2:
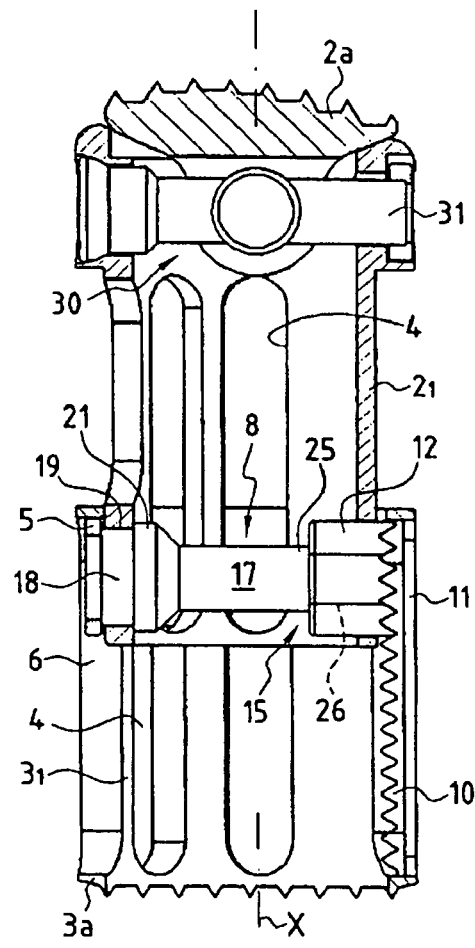
FIG. 2 is a cross-sectional elevation view showing the vertebral implant in a locking position.
Figure 3:
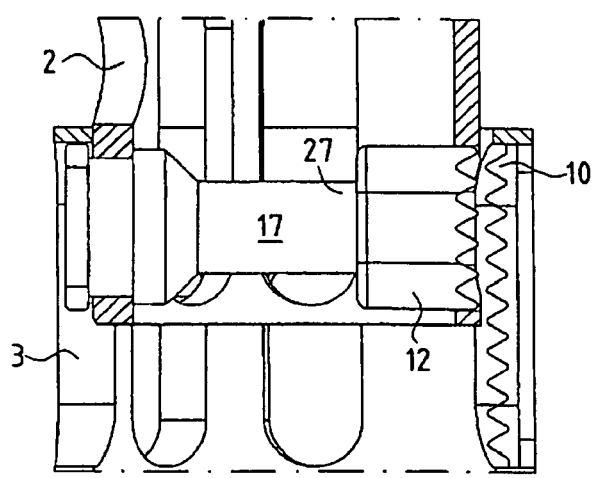
FIG. 3 is partial cross-sectional elevation view showing the implant in a position in which the elements slide freely with respect to each other.

According to one characteristic of the invention, the replacement implant 1 comprises means 8 ensuring firstly the free sliding of elements 2, 3 between each other and secondly their relative locking. These locking means 8 on one of the elements, namely the female element 3 in the illustrated example, comprise an anchor surface 10 arranged on a longitudinal part 11 of the wall. This anchor surface 10 extends inside the wall of the female element 3 opposite an anchor shoe 12 mounted on the other element, namely the male element 2 in the illustrated example. The anchor screw 12 is guided in translation to take up a first position in which the male 2 and female 3 elements can slide freely with respect to each other (FIG. 3) and a second position in which the anchor shoe 12 engages with the anchor surface 10 to lock elements 2, 3 in position (FIG. 2). For this purpose, the anchor shoe 12 on its transverse face extending perpendicular to the direction of translation of the shoe, comprises a complementary or conjugate anchor shape on the anchor surface 10 so that, by mutual cooperation, elements 2, 3 come to be locked in position. For example, the anchor shoe 12 and the anchor surface 10 have teeth extending transversely to the sliding direction of the anchor shoe 12.

According to a further characteristic of the invention, the locking means 8 also comprise a movement conversion system 15 converting a rotational movement into a translational movement which is transmitted to the anchor shoe 12 so that it takes up its released position or its cooperation position with the anchor surface 10. The conversion system 15 is fitted with means 16 for receiving an instrument, not shown, adapted for commanding system 15 in rotation in the two opposite directions. Therefore, in relation to the direction of the rotational command given by the command instrument, the anchor shoe 12 is able to take up one of its two characteristic positions.

In a preferred example of embodiment illustrated in the drawings, the conversion system 15 is of screw/nut type. In this preferred example of embodiment, the conversion system 15 comprises a pin 17 guided in rotation and locked in translation and mounted so that it extends diametrically inside the male element 2 in the part thereof which remains engaged in the female element at all times. Pin 17 comprises a first end 18 of straight circular section mounted with clearance in a bore 19 made in the wall of the male element 2. The first end 18 is edged on one side by a shoulder 21 and on the other side by an abutment 5. Pin 17 is therefore locked in translation by the abutment 5 and shoulder 21, while being guided in rotation.

Advantageously, the first end 18 of pin 17 is provided with receiving means 16 to receive the instrument commanding rotation of the pin. In the illustrated example, the receiving means 16 are formed of a prismatic hole arranged in the transverse face delimiting the first end of pin 17. The hole 16 leads into the open lumen opening into the outer face of the female element 3 so that the hole 16 is accessible from outside the implant, using a command instrument such as a screwdriver for example.

Pin 17 is provided with a threaded part 25 cooperating with tapping 26 on the anchor shoe 12 which is guided in translation and locked in rotation. In the illustrated example, the second end 27 of the pin 17 opposite the first end 18, is provided with the threaded part 25. Therefore, as can be seen more clearly FIG. 4, the anchor shoe 12 has a prismatic outer shape mounted inside a bore 28 of similar section in the wall of the male element 2 thereby ensuring guiding in translation and locking in rotation of the anchor shoe 12. As arises from the preceding description, the rotation of pin 17 in one direction allows sliding of the anchor shoe 12 drawing it towards the anchor surface 10, while rotation of pin 17 in an opposite direction leads to drawing away the anchor shoe 12 by translation with respect to the anchor surface 10.

According to a further characteristic of the invention, each male 2 and female 3 element is provided with an end wall $2_a$, $3_a$ intended to cooperate with a vertebral plateau. Preferably, each end wall $2_a$, $3_a$ is provided with notching to promote anchoring of the implant on over- and underlying vertebral plateaux.

According to a preferred variant of embodiment, at least one end wall, namely end wall $2_a$ carried by the male element 2 in the illustrated example is equipped with a system 30 ensuring its inclining in the anatomical sagittal plane, represented by reference S in the drawings. According to a preferred characteristic of embodiment, the inclining system 30 is of screw/nut type. This inclining system 30 comprises a threaded rod 31 guided in rotation and locked in translation to cooperate with a tapped ring 32 locked in rotation and connected to end wall 2$_a$ in the illustrated example. More precisely, the threaded rod 31 extends diametrically inside the male element 2 along a direction parallel to the direction of extension of pin 17. The threaded rod 31 is provided at one end with a head 34 passing via a passageway 35 through the wall of the male element 2. The other end of the threaded rod 31 is provided with a translation stop abutment 37. The threaded rod 31 cooperates with the tapped ring 32 which is provided on either side with extensions 32$_1$ engaged in complementary holes arranged in lugs 40 extending at right angles from end wall 2$_a$.

Figure 4:
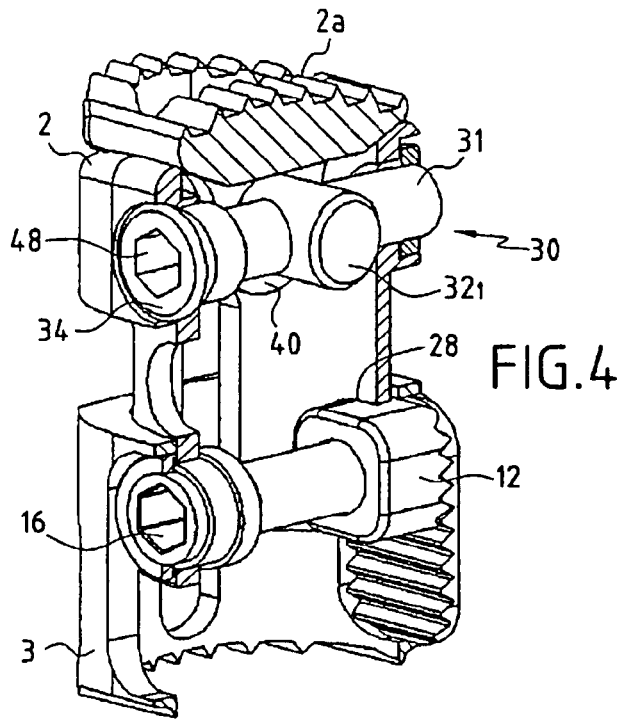
FIG. 4 is a partial cut-away, perspective view showing details characteristic of the subject of the invention.
Figure 5:
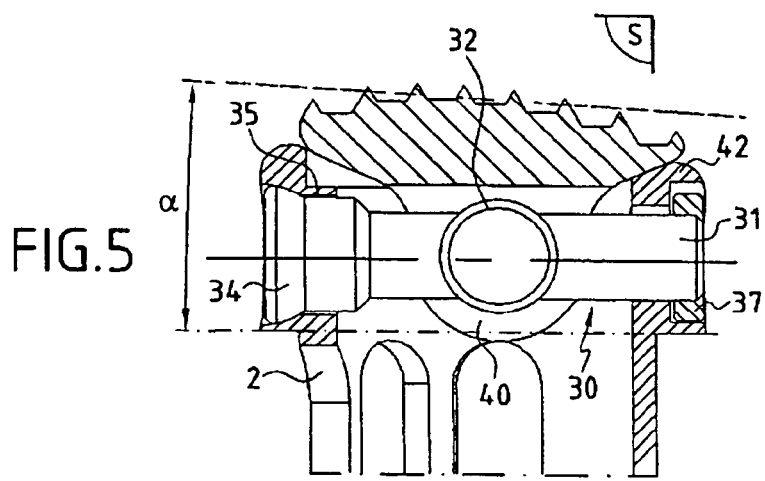
FIG. 5 is a cross-sectional elevation view of a preferred characteristic of the embodiment equipping a vertebral implant of the invention.

As can be seen more clearly FIGS. 4 and 5, the end wall 2$_a$ is carried by a plateau 42 extending from the body of the male element 2 and delimiting a cradle with its upper edge for the rotational guiding of the end wall 2$_a$. Therefore, end wall 2$_a$ has an inner convex face able to cooperate with the plateau 42 of concave shape.

As arises clearly from a comparison between FIGS. 2 and 4, rotation of the threaded rod 31 leads to translation of the tapped ring 32 which imposes rotation of the end wall 2$_a$ guided by the cradle of the male element 2. The end wall 2$_a$ can therefore be inclined at an angle α for example in the order of 5°.

According to a characteristic of the invention, the threaded rod 31 comprises receiving means 48 to receive a command instrument accessible from outside the male element 2. In the illustrated example, the receiving means 48 consist of a hole of prismatic section arranged in the transverse wall delimiting the head 34 of the threaded rod 31. The hole 48 is therefore accessible from outside the male element 2 and is preferably aligned with the receiving means 16 along a longitudinal direction. The receiving means 16 and 48 which occupy a close superimposed position, are preferably of identical shape so that they can be handled by one same command instrument, such as a screwdriver for example.

According to a further characteristic of the invention, the intervertebral implant 1 is adapted to ensure the easy, efficient sliding movement of the male 2 and female 3 elements. For this purpose, each male 2 and female 3 element comprises grasping zones 50 for a distractor 51 ensuring relative sliding between the male 2 and female 3 elements. These grasping zones 50 are made on each element via two flats extending in diametrically opposite fashion on the male 2 and female 3 elements.

Figure 6:
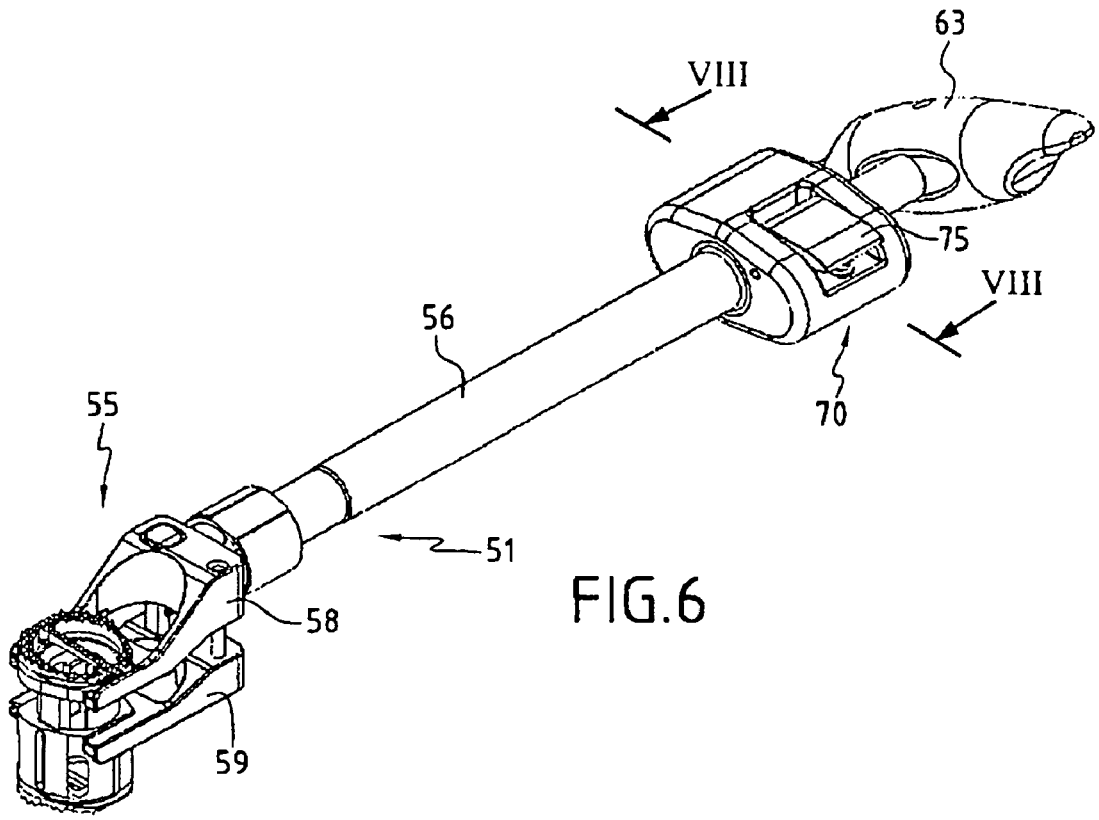
FIG. 6 is a perspective view showing a distractor for the implant according to the invention.
Figure 7:
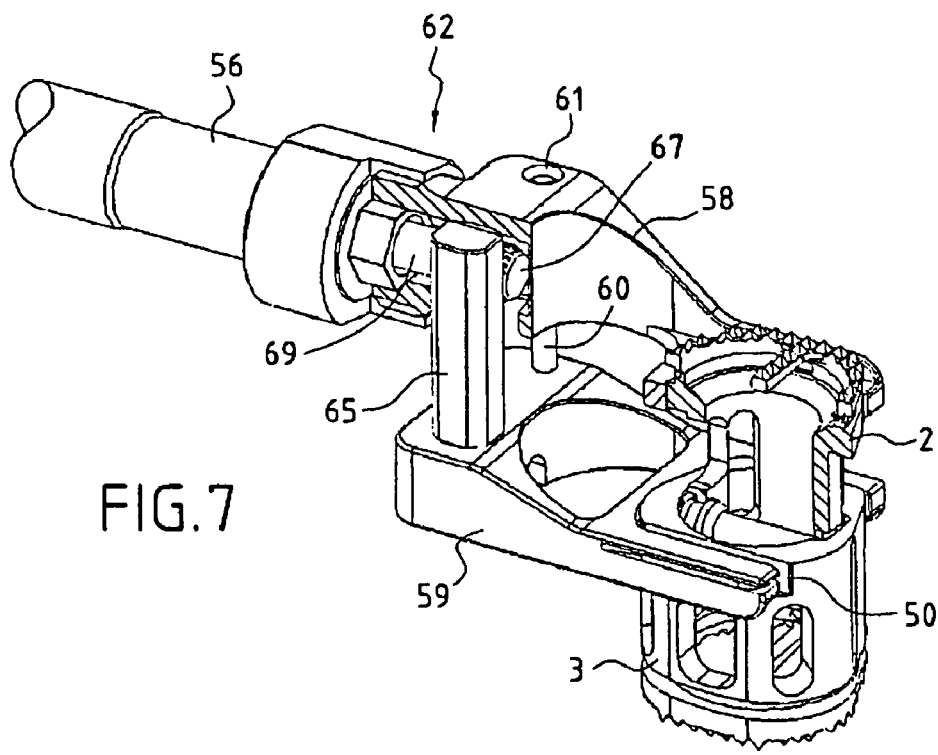
FIG. 7 is a partial cut-away, perspective view showing the cooperation between the distractor and the implant of the invention.

As can be seen more precisely FIGS. 6 and 7, the distractor 51 comprises a gripper head 55 extending from a tube 56. The head 55 comprises a fixed jaw 58 and a mobile jaw 59 intended to ensure the grasping of the male 2 and female 3 elements. Each jaw 58, 59 therefore delimits a U-shaped clamp intended to engage on the two diametrically opposite flats of an element 2, 3. The fixed jaw 58 is mounted integral with the tube 56, whilst the mobile jaw 59 is equipped with a guiding column 60 slidably mounted inside a guiding bore 61 arranged in the fixed jaw 58. The distractor 51 also comprises a system 62 for converting a rotational movement imposed by a handle 63, that is preferably removable, into a translational movement transmitted to the mobile jaw 59. Said conversion system 62 ensures relative spacing between the fixed jaw 58 and the mobile jaw 59 and subsequently between the male 2 and female 3 elements.

According to a preferred characteristic of embodiment, the conversion system 62 is ensured by a rack 65 connected to the mobile jaw 59 and cooperating with a toothed wheel 67 wedged in rotation with a command rod 69 extending inside the tube 56. Rotation in one direction of the rod 69 ensures relative spacing between the male 2 and female 3 element, whilst rotation in an opposite direction leads to relative drawing together of the male 2 and female 3 elements.

Figure 8:
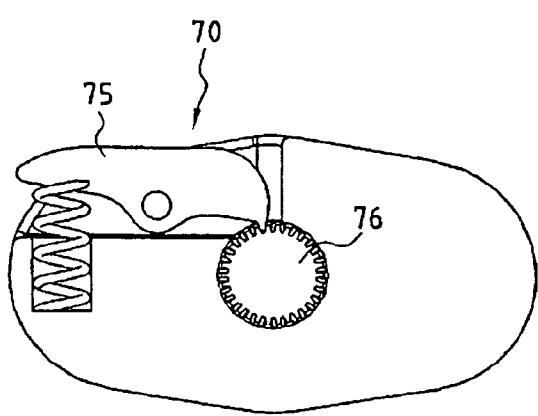
FIG. 8 is a cross-sectional view substantially along lines VIII-VIII in FIG. 6 and showing a characteristic detail of the subject of the invention.

According to a preferred characteristic of embodiment illustrated more precisely FIGS. 6 and 8, the conversion system 62 is equipped with a no-return device 70 preventing movement in a direction opposite to the spacing apart of the male 2 and female 3 elements. Preferably, said no-return device 70 can be released, thereby allowing movement in a direction in which the male 2 and female 3 elements are drawn together. Therefore, in a released position of the no-return device 70, the fixed and mobile jaws may be moved in both directions, namely spacing apart and drawing together.

As can be seen more clearly FIG. 8, the no-return device 70 consists for example of a manually activated pawl system 75 cooperating with a toothed wheel 76 mounted on the command rod 69. Pressing on the pawl 75 achieves release of the toothed wheel 76 thereby enabling movement of the rod 69 in a direction leading to the drawing together of the mobile 59 and fixed 58 jaws.

The invention is not limited to the examples described and illustrated since various modifications may be made thereto without departing from the scope of the invention.

The invention claimed is:

1. Vertebral replacement implant comprising:
   two hollow, longitudinal, generally tubular male and female elements, slidably mounted with respect to one another along a common longitudinal axis (X); and
   a device ensuring locking and free sliding of the elements with respect to each other, the locking device comprising:
   on the female element, an anchor surface arranged on a longitudinal part of a radially inner wall of said female element, said anchor surface fixed relative to said female element, and
   on the male element:
   an anchor shoe guided in translation to take up a first position in which the elements slide freely with respect to each other, and a second position in which the anchor shoe engages with the anchor surface to lock the elements together from moving along the X axis, the anchor shoe and anchor surface having selectively interlocking teeth configured to lock the elements together when interlocked, the interlocking teeth being longitudinally displaced in a direction extending transversely to a direction in which the anchor shoe can be translated,
   a screw nut-type conversion system for converting a rotational movement into a translational movement transmitted to the anchor shoe, the conversion system comprising a pin extending diametrically inside the male element and comprising:
   a first end provided with a receiving device to receive an instrument commanding rotation in two opposite directions such that the anchor shoe takes up one of the positions in relation to the direction of a rotation command of the instrument, the first end being guided in rotation and locked in translation in a wall of the male element, and
   a second end provided with a threaded part cooperating with a tapping of the anchor shoe, wherein rotation of the second end relative to the anchor shoe causes the anchor shoe to be guided in translation relative to said second end and said wall of said male element and locked in rotation in the wall of the male element, wherein the receiving device leads into a lumen opening in a wall of the female element so as to be accessible from outside the implant, the wall of the female element provided with the anchor surface being opposite the wall in which the lumen opens.

2. Vertebral replacement implant as in claim 1, wherein each of the male and the female element is provided with an end wall intended to cooperate with a vertebral plateau.

3. Vertebral replacement implant as in claim 2, wherein at least one end wall is equipped with a system for inclining the end wall in the sagittal plane.

4. Vertebral replacement implant as in claim 3, characterized in that the system for inclining the end wall is of screw/nut type and comprises a threaded rod guided in rotation and locked in translation to cooperate with a tapped ring locked in rotation and connected to the end wall guided in its incline.

5. Vertebral replacement implant as in claim 4, wherein the threaded rod extends diametrically inside one element and comprises means for receiving a command instrument accessible from outside the element.

6. Vertebral replacement implant as in claim 1, wherein each male and female element comprises grasping zones for a distracter ensuring the relative sliding between the male and female elements, the grasping zones being formed of two flats extending in diametrical opposite manner on the male and female elements.

7. Vertebral replacement implant as in claim 1, additionally comprising a plateau extending from the male element, and delimiting a cradle for rotational guiding of an end wall of the male element.

8. Vertebral replacement implant as in claim 1, wherein said anchor surface defines said teeth thereon.

9. Vertebral replacement implant as in claim 1, wherein said anchor surface is unitary in structure with said teeth thereon.

10. Vertebral replacement implant as in claim 1, wherein said anchor shoe is moveable relative to said second end of said pin.

\* \* \* \* \*